United States Patent [19]

Hoshino et al.

[11] Patent Number: 5,766,894
[45] Date of Patent: Jun. 16, 1998

[54] PRODUCTION OF VITAMIN $B_6$ BY FERMENTATION

[75] Inventors: Tatsuo Hoshino, Kamakura; Keiko Ichikawa, Fujisawa; Masaaki Tazoe, Yokohama, all of Japan

[73] Assignee: Roche Vitamins Inc., Parsippany, N.J.

[21] Appl. No.: 709,068

[22] Filed: Sep. 6, 1996

[30] Foreign Application Priority Data

Sep. 30, 1995 [EP] European Pat. Off. ............ 95115488

[51] Int. Cl.$^6$ .................................................. C12P 17/12
[52] U.S. Cl. ........................................ 435/122; 435/252.2
[58] Field of Search ............................... 435/122, 252.2

[56] References Cited

PUBLICATIONS

Chem Abs 88:018836(03) Begishuili et al. "Soobshch Akad Nauk Gruz SSR" 87(2)1977 pp. 465–467.
ACS Caplus 1967:507740 Ratner et al. VCH Zap Tartu Gos. Univ. (1966) No. 185 pp. 216–227.
ACS Caplus 1968:474622 Shemakhanova et al "Mikrobiolgiya" (1968) vol. 37 No. 3 pp. 433–439.
ACS Caplus 1972:45262 Shemakhanova et al "Mikrobiologiya" (1972) vol. 41 No. 2 pp. 256–259.
ACS Caplus 1972:458924 Begishuili "Soobshch. Akad Vauk Gruz SSR" 1972 Vol. 66 No. 2 pp. 461–463.
ACS Caplus 1974:550221 Samtsevich et al "Ispoliz Mikroorg. Ikh. Netab. Khoz." 1973 pp. 79–83.
ACS Caplus 1975:404617 Samtsevich et al "Ekol. Pochv. Mikroorg." 1974 3–6.
Hill, R.E., et al., *J. Am. Chem. Soc.*, 111:1916–1917 (1989).
Iwanow, A., et al., *J. Am. Chem. Soc.*, 106:1840–1841 (1984).
Kennedy, I., et al., *J. Am. Chem. Soc.*, 117:1661–1662 (1995).
Matsuura, M., et al., *Agric. Biol. Chem.*, 46(8):2127–2133 (1982).
Bella, G., et al., *The Journal of Biological Chemistry*, 225(7):3042–3048 (1980).
Wolf, E., et al., *J. Chem. Soc. Chem. Commun.*, No. 13:1339–1340 (1995).
Dempsey, W.B., *J. Bacteriology*, 93(3):1179–1180 (1967).
Ishida, M. and K. Shimura, *Agr. Biol. Chem.*, 34(4):327–334 (1970).
Morris, J.G., *J. Gen. Microbiol.*, 20:597–604 (1959).
Nishio, N., et al., *Agr. Biol. Chem.*, 37(3):553–339 (1973).
Osborne, D.R. and P. Voogt, "The Analysis of Nutrients in Foods", Academic Press, London, pp. 224–227 (1978).
Pardini, R.S. and C.J. Argoudelis, *J. Bacteriology*, 96(3):672–277 (1968).
Scherr, G.H. and M.E. Rafelson, *J. Appl. Bact.*, 25(2):187–194 (1962).
Suzue, R. and Y. Haruna, *J. Vitaminology*, 16:154–159 (1970).
Tani, Y., et al., *Agr. Biol. Chem.*, 36(2):189–197 (1972).
Tsuge, H., and N. Hirose, *Vitamins: Journal of the Vitamin Society of Japan*, 63(8):349–368 (1989).

*Primary Examiner*—Herbert J. Lilling
*Attorney, Agent, or Firm*—George W. Johnston; Dennis P. Tramaloni; Alan P. Kass

[57] ABSTRACT

A process for producing vitamin $B_6$ comprises cultivating a microorganism belonging to the genus Rhizobium and being capable of producing vitamin $B_6$ in a culture medium under aerobic conditions, and separating the resulting vitamin $B_6$ from the fermentation broth. As well as containing assimilable carbon sources, digestible nitrogen sources, inorganic salts and other nutrients necessary for the growth of the microorganism, the culture medium preferably additionally contains pyruvate, D-glyceraldehyde, glycolaldehyde, glycine, 1-deoxy-D-threo-pentulose, 4-hydroxy-L-threonine or a mixture thereof. This process affords high yields of vitamin $B_6$, a vitamin essential for the nutrition of animals, plants and microorganisms and useful as a medicine and in foodstuffs.

12 Claims, No Drawings

PRODUCTION OF VITAMIN $B_6$ BY FERMENTATION

This invention relates to a process for the production of vitamin $B_6$ by fermentation. "Vitamin $B_6$" as used in the present application includes pyridoxol, pyridoxal and pyridoxamine.

Vitamin $B_6$ is essential for the nutrition of animals, plants and microorganisms, and is used as a medicine and in foodstuffs. An object of the present invention is to provide a ferment production of vitamin $B_6$ of high efficiency.

There are many studies on the production of vitamin $B_6$, and various microorganisms belonging to the genera Saccharomyces, Pichia, Klebsiella, Achromobacter, Bacillus and Flavobacterium are known to produce vitamin $B_6$. But the accumulation of a large amount of vitamin $B_6$ by the microorganisms belonging to the genus Rhizobium has never been reported.

The present invention makes it is possible to produce vitamin $B_6$, in high yield. It has been found that the microorganisms belonging to the genus Rhizobium are capable of accumulating a large amount of vitamin $B_6$ in the culture broth that can be recovered therefrom in a desired purity.

The present invention is thus concerned with a process for producing vitamin $B_6$ which comprises cultivating a microorganism belonging to the genus Rhizobium and being capable of producing vitamin $B_6$ in aqueous culture medium under aerobic conditions, and separating the resulting vitamin $B_6$ from the fermentation broth.

The content of vitamin $B_6$ in a fermentation broth can be assayed with *Saccharomyces carlsbergensis* ATCC 9080 [The Analysis of Nutrients in Foods, Academic Press, London, 224–227 (1978)], and the content of vitamin $B_6$ components such as pyridoxol, pyridoxal and pyridoxamine in a fermentation broth can also be measured separately by high performance liquid chromatography [Vitamin, 63, 349–369 (1989)].

For carrying out the present invention, microorganisms belonging to the genus Rhizobium are incubated in aqueous culture medium containing assimilable carbon sources, digestible nitrogen sources, inorganic salts and other nutrients necessary for the growth of the microorganism. As the carbon source, for example, glucose, fructose, lactose, galactose, sucrose, maltose, starch, dextrin or glycerol may be employed. As the nitrogen source, for example, peptone, soybean powder, corn steep liquor, meat extract, ammonium sulfate, ammonium nitrate, urea or mixtures thereof may be employed. Further, as the inorganic salts, sulfates, hydrochlorides or phosphates of calcium, magnesium, zinc, manganese, cobalt and iron may be employed. And, if necessary, conventional nutrient factors or an antifoaming agent such as animal oil, vegetable oil or mineral oil can also be added. The pH of the culture medium is suitably from about 5.0 to about 9.0, preferably from about 6.5 to about 7.5. The cultivation temperature is suitably from about 10° to about 40° C., preferably from about 26° to about 30° C. The cultivation time is suitably from about 1 to about 14 days, preferably from about 2 to about 7 days. In the cultivation, aeration and agitation usually give favorable results. The presence of a compound selected from pyruvate, D-glyceraldehyde, glycolaldehyde, glycine, 1-deoxy-D-threo-pentulose, 4-hydroxy-L-threonine and an appropriate combination thereof in the medium gives more favorable results for the vitamin $B_6$ titer and is therefore preferred. The combination of 1-deoxy-D-threo-pentulose and 4-hydroxy-L-threonine is particularly effective as such a supplement for the production of vitamin $B_6$.

The production of vitamin $B_6$ can also be achieved by incubating cells of microorganisms belonging to the genus Rhizobium separated from the culture broth in a buffer of proper pH value with appropriate combination of pyruvate, D-glyceraldehyde, glycolaldehyde, glycine, 1-deoxy-D-threo-pentulose and 4-hydroxy-L-threonine. After the cultivation, produced vitamin $B_6$ may be separated from the culture broth and purified. For this purpose, a process used for isolating product from the culture broth may be applied by utilizing various properties of vitamin $B_6$. Thus, for example, after the cells have been removed from the culture broth, the desired substance in the filtrate is purified using an ion exchange resin or similar means. After the elution, the desired product is recrystallized from alcohol.

The microorganism used according to the present invention includes all strains belonging to the genus Rhizobium which are capable of producing vitamin $B_6$ and which are preserved in a public depository (culture collection) for availability to anyone upon request, such as the Institute of Fermentation Osaka, Japan (IFO), the Ministry of Agriculture, Forestry and Fishery, Japan (MAFF) or the Institute of Applied Microbiology, the University of Tokyo, Japan (IAM); Example of such deposited strains are *Rhizobium meliloti* IFO 14782, *Rhizobium meliloti* MAFF 303040, *Rhizobium meliloti* MAFF 303047, *Rhizobium meliloti* MAFF 303097, *Rhizobium tropici* IFO 15247, *Rhizobium huakuii* IFO 15243, *Rhizobium leguminosarum* IFO 14778, *Rhizobium galegae* IFO 14965, *Rhizobium fredii* IFO 14780, *Rhizobium loti* IFO 14998, Rhizobium sp. IAM 13623 and Rhizobium sp. IAM 13631. Among these strains of the genus Rhizobium particularly preferred ones are *Rhizobium meliloti* IFO 14782 and *Rhizobium tropici* IFO 15247. The strains *Rhizobium meliloti* IFO 14782 and *Rhizobium tropici* IFO 15247 were also deposited at the DSM (Deutsche Sammlung von Mikroorganismen und Zellkulturen GmbH) in Göttingen, Germany under DSM No. 10226 and No. 10227, respectively, on Sep. 4, 1995.

The present invention is illustrated in more detail by the following Examples.

EXAMPLE 1

A loopful of cells of *Rhizobium meliloti* IFO 14782 (DSM No. 10226) grown on the agar medium composed of 0.1% yeast extract (Difco), 0.5% mannitol, 0.07% $KH_2PO_4$, 0.01% $KH_2PO_4$, 0.1% $MgSO_4 \cdot 7H_2O$ and 1.5% agar (pH 7.0) was inoculated into a tube containing 5 ml of the seed medium consisting of 1% glucose, 0.5% polypeptone (Nippon Seiyaku Co., Japan), 0.2% yeast extract (Difco), 0.1% $KH_2PO_4$, 0.05% $MgSO_4 \cdot 7H_2O$, 0.001% $MnSO_4 \cdot 5H_2O$ and 0.001% $FeSO_4 \cdot 7H_2O$, and then the tube was shaken on a reciprocal shaker (285 rpm) at 28° C. for 17 hours. 4 ml of the seed culture were inoculated into a 500-ml flask with 2 baffles containing 200 ml of the culture medium comprising 4% glucose, 4% polypeptone S (Nippon Seiyaku Co., Japan), 0.8% yeast extract (Difco), 0.05% $MgSO_4 \cdot 7H_2O$, 0.05% $MnSO_4 \cdot 5H_2O$, 0.001% $FeSO_4 \cdot 7H_2O$ and one drop of antifoam CA-115 (Nippon Yushi Co., Japan), and then the flask was cultured with rotary shaking (180 rpm) at 28° C. After cultivation for 168 hours, the content of vitamin $B_6$ in the supernatant of the culture broth was assayed by the turbidity method with *Saccharomyces carlsbergensis* ATCC 9080 as described below. The supernatant and standard solutions of pyridoxol (0–100 mg per liter) were serially diluted to $1.731 \times 10^{-4}$ in distilled water. 200 μl of the diluted solution, 1.5 ml of distilled water and 40 μl of 1.155N $H_2SO_4$ were added to tubes in this order.

After autoclaving at 120° C. for 20 minutes, 1.5 ml of the assay medium for vitamin $B_6$ (Nissui Co., Japan) containing *Saccharomyces carlsbergensis* ATCC 9080 were added to the tubes, and incubated with an angle of 30° at 28° C. After incubation for 17 hours, the cell growth was stopped by adding 5 ml of 0.2N hydrochloric acid, and then the absorbance of the samples was measured at 660 nm. The amount of vitamin $B_6$ in a sample was determined by comparing the turbidity of the sample with the standard growth curve of *Saccharomyces carlsbergensis* ATCC 9080. As a result, the supernatant of 168 hours culture broth contained 84 mg of vitamin $B_6$ per liter. Furthermore, after 100 μl of 4'-deoxypyridoxol (100 mg per liter) as internal substance had been added to 400 μl of the supernatant of 168 hours culture broth, the mixture was analyzed on a Capcell pak $C_{18}$ SG120 column (4.6×250 mm, Shiseido Co., Japan) with the mixed solvent of 0.1M sodium perchlorate, 0.1M potassium phosphate and 2% acetonitrile (pH 3.5) at a flow rate of 1.0 ml/minute at λ=292 nm by the HPLC system consisting of a Waters Model 600E system controller, a Waters Model 600F pump, a Waters Model 991J photodiode array detector, a Waters Model 700 satellite WISP sample injector and a Waters 5200 printer. As a result, it was found that the supernatant contained 78.6 mg of pyridoxol per liter.

EXAMPLE 2

In a similar manner as described in Example 1, *Rhizobium meliloti* MAFF 303040, *Rhizobium meliloti* MAFF 303047, *Rhizobium meliloti* MAFF 303097, *Rhizobium huakuii* IFO 15243, *Rhizobium leguminosarum* IFO 14778, *Rhizobium tropici* IFO 15247 (DSM No. 10227), *Rhizobium galegae* IFO 14965, *Rhizobium fredii* IFO 14780, *Rhizobium loti* IFO 14998, Rhizobium sp. IAM 13623 and Rhizobium sp. IAM 13631 were cultivated. After cultivation in each case for 168 hours, the content of vitamin $B_6$ in the supernatant of the culture broth was assayed by the turbidity method with *Saccharomyces carlsbergensis* ATCC 9080. The results are shown in Table 1.

TABLE 1

Production of Vitamin $B_6$ by Rhizobium Strains

| Rhizobium strain | Vitamin $B_6$ (mg/L) |
| --- | --- |
| *Rhizobium meliloti* MAFF 303040 | 10.8 |
| *Rhizobium meliloti* MAFF 303047 | 30.5 |
| *Rhizobium meliloti* MAFF 303097 | 11.6 |
| *Rhizobium huakii* IFO 15243 | 19.7 |
| *Rhizobium leguminosarum* IFO 14778 | 9.85 |
| *Rhizobium tropici* IFO 15247 | 9.00 |
| *Rhizobium galegae* IFO 14965 | 7.81 |
| *Rhizobium fredii* IFO 14780 | 4.02 |
| *Rhizobium loti* IFO 14998 | 10.3 |
| Rhizobium sp. IAM 13623 | 6.70 |
| Rhizobium sp. IAM 13631 | 5.11 |

EXAMPLE 3

Vitamin $B_6$ was recovered from the culture broth of *Rhizobium meliloti* IFO 14782 (DSM No. 10226) prepared under the same culturing conditions as described in Example 1. The vitamin $B_6$ concentration at each purification step was followed by the turbidity method with *Saccharomyces carlsbergensis* ATCC 9080. One liter of the 168 hours culture broth was centrifuged at 8,000 rpm for 10 minutes. The pH of the resultant supernatant was adjusted to 3.1 with 1N hydrochloric acid, and then the supernatant was applied to a column (3.6×40 cm) packed with 350 ml of Amberlite CG 120 ($H^+$ form, 100–200 mesh, Organo Co. Ltd). The column was washed with 300 ml of deionized water and then eluted with 5% ammonium hydroxide. The vitamin $B_6$ fractions were concentrated under reduced pressure. The residue thus obtained was dissolved in 10 ml of 0.01M ammonium formate (pH 3.2), and the solution was charged on a column (2.4×40 cm) packed with 180 ml of Dowex 50 w×8 (ammonium form, 200–400 mesh, Dow Chemical Co. Ltd., U.S.A.), and then washed with 200 ml of 0.01M ammonium formate (pH 3.2). The column was then developed with 200 ml of the starting buffer of 0.05M ammonium formate (pH 4.25) and followed by the linear gradient of 200 ml each of 0.05 and 0.5M ammonium formate (pH 7.0) buffer.

The chromatogram gave one major and 2 minor peaks having the growth activity against *Saccharomyces carlsbergensis* ATCC 9080. The fraction of the major peak was concentrated to small volume under reduced pressure, the pH of the solution was adjusted to 3.1 with 1N hydrochloric acid, and then the solution was applied to a column (1.8×40 cm) packed with 75 ml of Amberlite CG 120 ($H^+$ form, 100–200 mesh). The column was washed with 150 ml of deionized water and then eluted with 5% ammonium hydroxide. The fractions having the growth activity against *Saccharomyces carlsbergensis* ATCC 9080 were concentrated under reduced pressure. After the solid residue had been dissolved in a small amount of hot ethanol, the solution was kept standing at 4° C. overnight. The resultant precipitates were collected by filtration and dried in vacuo to obtain 51 mg of crude crystals. These were recrystallized from ethanol to obtain 44 mg of white crystals having a melting point of 160° C. The infrared absorption, UV absorption and NMR spectra of the product coincided with those of authentic pyridoxol. Two minor peaks having the growth activity against *Saccharomyces carlsbergensis* ATCC 9080 were analyzed by HPLC under the analytical conditions as described in Example 1, and were identified as pyridoxamine and pyridoxal, respectively.

EXAMPLE 4

Seed culture of *Rhizobium tropici* IFO 15247 (DSM No. 10227) was prepared under the same culturing conditions as described in Example 1.4 ml of the seed culture were inoculated into two 500-ml flasks containing 200 ml of the culture medium comprising 2% glucose, 1% polypeptone, 0.2% yeast extract, 0.05% $MgSO_4.7H_2O$, 0.05% $MnSO_4.5H_2O$, 0.001% $FeSO_4.7H_2O$ and one drop of antifoam CA-115. Further, 4 ml of the sterilized solution containing 1% 1-deoxy-D-threo-pentulose (referred to as DTP hereafter) and 1% 4-hydroxy-L-threonine (referred to as HT hereafter) were added to one flask, and 4 ml of sterilized water to the other. Both flasks were shaken on a rotary shaker (180 rpm) at 28° C. After cultivation for 96 hours at 28° C., the content of vitamin $B_6$ in the supernatant of the culture broth was assayed by the turbidity method with *Saccharomyces carlsbergensis* ATCC 9080 as described in Example 1. As summarized in Table 2, 45 mg of vitamin $B_6$ per liter were produced in the flask containing the medium supplemented with DTP and HT, whereas 3.16 mg of vitamin $B_6$ per liter were produced in the flask containing the medium without DTP and HT. Furthermore, from one liter of the 96 hours culture broth in the medium supplemented with 0.02% each DTP and HT, the product was isolated by the same method as described in Example 3 to obtain 19.3 mg of white crystals having a melting point of 159.5° C. The infrared absorption, UV absorption and NMR spectra of the product coincided with those of authentic pyridoxol.

TABLE 2

Production of Vitamin $B_6$ by *Rhizobium tropici* IFO 15247 (DSM No. 10227)

| Medium | Vitamin $B_6$ (mg/L) |
| --- | --- |
| Medium supplemented with DTP and HT | 45.0 |
| Medium without DTP and HT | 3.16 |

DTP: 1-deoxy-D-threo-pentulose, HT: 4-hydroxy-L-threonine

EXAMPLE 5

*Rhizobium meliloti* IFO 14782 (DSM No. 10226) was cultivated under the same culturing conditions as described in Example 1. After cultivation for 72 hours at 28° C., the cells were collected by centrifugation at 8,000 rpm for 10 minutes, washed twice with 100 ml of sterile 0.85% sodium chloride solution and suspended in 88 ml of sterile distilled water. The vitamin $B_6$ production was carried out with reciprocal shaking (285 rpm) at 28° C. in a tube containing 10 ml of 0.1M Tris-HCl buffer (pH 8.0) composed of 0.02% DTP, 0.24% glycolaldehyde, 0.24% glycine and the cell suspension (final optical density at 600 nm=20/ml). After shaking for 24 hours at 28° C., vitamin $B_6$ in the supernatant of the reaction mixture was determined by HPLC under the analytical conditions as described in Example 1. As summarized in Table 3, 9.66 mg of pyridoxol per liter were produced from DTP, glycolaldehyde and glycine.

TABLE 3

Production of Pyridoxol from DTP, Glycolaldehyde and Glycine by *Rhizobium meliloti* IFO 14782 (DSM No. 10226)

| Substrate | Pyridoxol (mg/L) |
| --- | --- |
| DTP + Glycolaldehyde + Glycine | 9.66 |
| None | 0 |

DTP: 1-deoxy-D-threo-pentulose

EXAMPLE 6

The washed cell suspension of *Rhizobium meliloti* IFO 14782 (DSM No. 10226) was prepared by the same method as described in Example 5. The vitamin $B_6$ production was carried out with reciprocal shaking (285 rpm) at 28° C. in a tube containing 10 ml of 0.1M Tris-HCl buffer (pH 7.6) comprising 0.24% pyruvate, 0.24% D-glyceraldehyde, and 0.02% HT and the washed cell suspension (final optical density at 600 nm=20/ml). After shaking for 24 hours at 28° C., vitamin $B_6$ in the supernatant of the reaction mixture was determined by HPLC under the analytical conditions as described in Example 1. As summarized in Table 4, 10.1 mg of pyridoxol per liter were produced from pyruvate, D-glyceraldehyde and HT.

TABLE 4

Production of Pyridoxol from Pyruvate, D-Glyceraldehyde, and HT by *Rhizobium meliloti* IFO 14782 (DSM No. 10226)

| Substrate | Pyridoxol (mg/L) |
| --- | --- |
| pyruvate + D-glyceraldehyde + HT | 10.1 |
| None | 0 |

HT: 4-hydroxy-L-threonine

EXAMPLE 7

The washed cell suspension of *Rhizobium meliloti* IFO 14782 (DSM No. 10226) was prepared by the same method as described in Example 5. The vitamin $B_6$ production was carried out with reciprocal shaking at 285 rpm at 28° C. in a tube containing 10 ml of 0.1M Tris-HCl buffer (pH 8.0) comprising 0.24% pyruvate, 0.24% D-glyceraldehyde, 0.24% glycolaldehyde, 0.24% glycine and the washed cell suspension (final optical density at 600 nm=20/ml). After incubation for 24 hours at 28° C., vitamin $B_6$ in the supernatant of the reaction mixture was determined by HPLC under the analytical conditions as described in Example 1. As summarized in Table 5, 9.66 mg of pyridoxol per liter were produced from pyruvate, D-glyceraldehyde, glycolaldehyde and glycine.

TABLE 5

Production of Pyridoxol from Pyruvate, D-Glyceraldehyde, Glycolaldehyde and Glycine by *Rhizobium meliloti* IFO 14782 (DSM No. 10226)

| Substrate | Pyridoxol (mg/L) |
| --- | --- |
| pyruvate + D-glyceraldehyde + glycolaldehyde + glycine | 9.66 |
| None | 0 |

We claim:

1. A process for producing vitamin $B_6$ which comprises:
   (a) cultivating under aerobic conditions in an aqueous culture medium containing assimilable sources of carbon and nitrogen, an inorganic salt selected from the group consisting of sulfates, hydrochlorides or phosphates of calcium, magnesium, zinc, manganese, cobalt and iron, and mixtures thereof, and a compound selected from the group consisting of pyruvate, D-glyceraldehyde, glycolaldehyde, glycine, 1-deoxy-D-threo-pentulose, 4-hydroxy-L-threonine and combinations thereof a microorganism belonging to the genus Rhizobium which is capable of producing vitamin $B_6$, so as to produce vitamin $B_6$; and
   (b) recovering the vitamin $B_6$ produced.

2. The process of claim 1 wherein the microorganism belonging to the genus Rhizobium is selected from the group consisting of *Rhizobium meliloti* IFO 14782 DSM No. 10226, *Rhizobium tropici* IFO 15247 DSM No. 10227, *Rhizobium huakuii* IFO 15243, *Rhizobium leguminosarum* IFO 14778, *Rhizobium galegae* IFO 14965, *Rhizobium fredii* IFO 14780, and *Rhizobium loti* IFO 14998.

3. The process of claim 2 wherein the microorganism belonging to the genus Rhizobium is selected from the group consisting of *Rhizobium meliloti* IFO 14782 DSM No. 10226 and *Rhizobium tropici* IFO 15247 DSM No. 10227.

4. The process of claim 3 wherein the microorganism belonging to the genus Rhizobium is *Rhizobium meliloti* IFO 14782 (DSM No. 10226).

5. The process of claim 3 wherein the microorganism belonging to the genus Rhizobium is *Rhizobium tropici* IFO 15247 (DSM No. 10227).

6. The process of claim 1 wherein the compound is a combination of 1-deoxy-D-threo-pentulose and 4-hydroxy-L-threonine.

7. The process of claim 1 wherein the pH of the culture medium is from about 5.0 to about 9.0.

8. The process of claim 7 wherein the pH of the culture medium is from about 6.5 to about 7.5.

9. The process of claim 7 wherein the cultivation is performed at a temperature of from about 10° C. to about 40° C.

10. The process of claim 9 wherein the cultivation is performed at a temperature of from about 26° C. to about 30° C.

11. The process of claim 9 wherein the cultivation is performed at a time of from about 1 to about 14 days.

12. The process of claim 11 wherein the cultivation is performed at a time of from about 2 to about 7 days.

\* \* \* \* \*